United States Patent [19]

Meno et al.

[11] Patent Number: 4,484,579
[45] Date of Patent: Nov. 27, 1984

[54] COMMISSUROTOMY CATHETER APPARATUS AND METHOD

[75] Inventors: Frank Meno; P. S. Reddy, both of Pittsburgh, Pa.

[73] Assignee: University of Pittsburgh, Pittsburgh, Pa.

[21] Appl. No.: 399,864

[22] Filed: Jul. 19, 1982

[51] Int. Cl.³ .............................................. A61F 17/32
[52] U.S. Cl. ................................. 128/305; 128/344; 128/749; 604/101
[58] Field of Search ............ 128/305, 344, 348.1, 128/749, 751, 757, 309, 361; 604/96–99, 101–104

[56] References Cited

U.S. PATENT DOCUMENTS

| | | | |
|---|---|---|---|
| 2,701,559 | 2/1955 | Cooper | 128/344 X |
| 3,045,677 | 7/1962 | Wallace | 128/349 |
| 3,154,077 | 10/1964 | Cannon | 128/325 |
| 3,411,506 | 11/1968 | Velasco | 604/101 X |
| 4,091,816 | 5/1978 | Elam | 128/351 |
| 4,271,839 | 6/1981 | Fogarty et al. | 128/344 |
| 4,273,128 | 6/1981 | Lary | 128/305 |
| 4,285,341 | 8/1981 | Pollack | 128/214 R |
| 4,292,976 | 10/1981 | Banka | 128/656 |
| 4,295,464 | 10/1981 | Shihata | 128/1 R |

Primary Examiner—Kyle L. Howell
Assistant Examiner—Christine A. Fukushima
Attorney, Agent, or Firm—Arnold B. Silverman

[57] ABSTRACT

A commissurotomy catheter and method for separating fused heart valve leaflets using the catheter is disclosed. The catheter is comprised of a lumen having at least two inflatable balloons at its operational end and at least one cutting edge between the balloons. To separate the fused leaflets the catheter is positioned within the heart so that it extends through the fused leaflets with a balloon on either side of the leaflets. Then the balloons are inflated which forces the cutting edge against the fissure between the fused leaflets and separates them. After separation the balloons are deflated and the catheter is removed.

11 Claims, 15 Drawing Figures

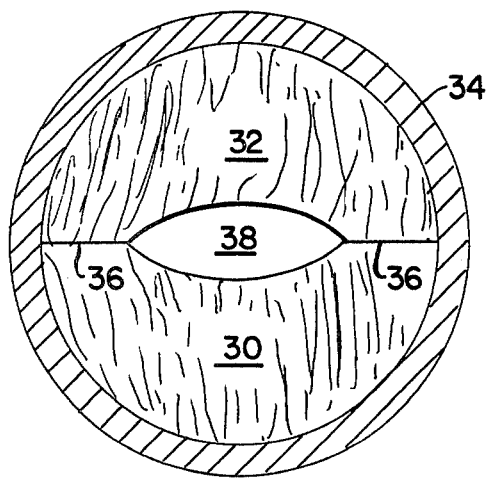
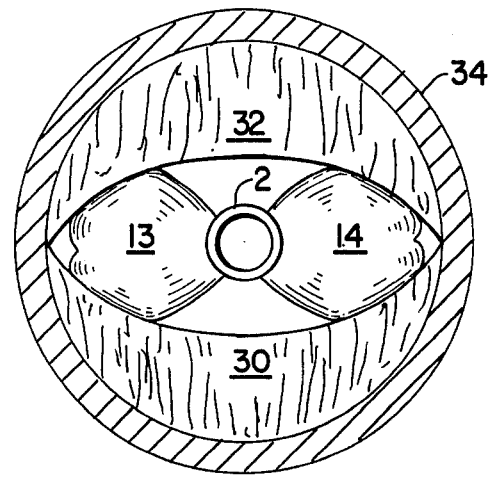
FIG. 5　　　　　　　　　FIG. 6
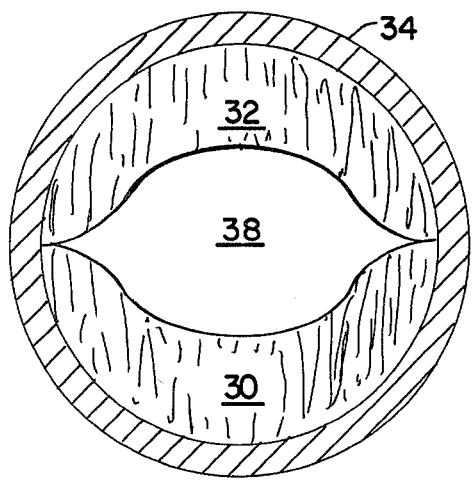
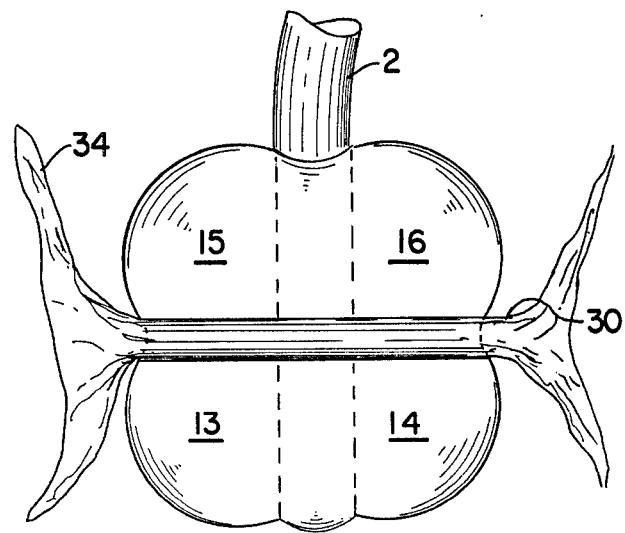
FIG. 7　　　　　　　　　FIG. 8

COMMISSUROTOMY CATHETER APPARATUS AND METHOD

BACKGROUND OF THE INVENTION

1. Field Of The Invention

The invention relates to a catheter apparatus for use in separating the two leaflets of the mitral valve of the heart during a surgical procedure known as a commissurotomy.

2. Description of the Prior Art

In certain types of heart diseases the leaflets of the heart valves fuse together near the valve orifice obstructing the flow of blood. If the condition is severe the current medical practice is to replace the damaged valve with an artificial valve. Insertion of an artificial heart valve requires major surgical intervention. Thereafter, the patient must remain chronically on drugs to prevent complications from hemolysis.

Heart surgeons have developed another surgical procedure called commissurotomy to correct fused heart valve leaflets or commissures. This procedure involves opening the chest, stopping the heart and cutting the fused leaflets apart. Although commissurotomy has been fairly successful it is a major surgical procedure.

Catheters have long been used for a variety of purposes in the blood vessels and other passageways in the body. Generally catheters are elongated flexible tubes inserted into a person's body to withdraw or inject fluids. A special type catheter frequently used to close a passageway is comprised of a lumen with one or more inflatable balloons at one end. When inflated the balloon presses against the walls of the passageway. Cannon in U.S. Pat. No. 3,154,077 discloses a balloon type catheter for post operative use in ano-rectal surgery. Wallace in U.S. Pat. No. 3,045,677 uses a similar catheter in the uretha. A tracheal tube having balloons to occupy the spaces above and below the open larynx is disclosed in U.S. Pat. No. 4,091,816. Shihata in U.S. Pat. No. 4,295,464 discloses a ureteric stone extractor having a dislodger balloon. Balloon type catheters for opening blood vessels are disclosed in U.S. Pat. Nos. 4,271,839 and 4,273,128. Pollack in U.S. Pat. No. 4,285,341 reveals a balloon type catheter for use during cardiac cannulation. Banka in U.S. Pat. No. 4,292,976 uses a catheter having a balloon tip to inject dye into the right ventricle of the heart.

Despite the wide variety of catheters in the prior art none are suitable for correcting damaged heart valves.

SUMMARY OF THE INVENTION

We have developed a commissurotomy catheter which will enable heart surgeons to separate fused heart valve leaflets without opening the chest and thereby avoid many of the risks of major surgery. The catheter is comprised of an elongated lumen sized to fit into a major vein or artery. At the end of the catheter we provide a strong pliable cutting edge preferably made of nylon or similar string. The ends of the cutting edge are attached to inflatable pockets or "balloons" on the lumen. These balloons are inflated by injecting saline or other suitable fluid through the lumen. Thus, the cutting edge is driven by inflation and deflation of the balloons.

We prefer to provide four balloons and two cutting edges. They are positioned on the lumen so that a pair of balloons is associated with each cutting edge and when the balloons are inflated the cutting edges are approximately opposite one another.

We further prefer to provide a means for selectively inflating the balloons. This can be accomplished by providing a second lumen (or more lumens if desired) within the catheter which is directly connected to a selected balloon or balloons.

To separate fused leaflets with our four balloon device, the catheter is inserted into the blood vessel and positioned so that two balloons are in the ventricle and two are in the atrium. As the balloons are expanding, they force the cutting edges to line up along the fissures and then continue to exert force on the commissures, thus separating the leaflets.

In some instances the force of the expanding balloons may not be adequate to separate the leaflets. Therefore, we prefer to design our catheter so that the balloons can be vibrated or inflated and deflated in a manner so that the cutting edges extending between the balloons will rock and act like a saw or pulsate and act like an axe. This sawing or chopping action can be obtained either by providing lumens in the catheter which can feed the liquid out of phase to the opposing balloons or by channeling the liquid in a manner so that the filling lag provides a phase shift which drives the cutting edge at a certain frequency.

Other details and advantages of our commissurotomy catheter and procedures for using the same will become apparent as the following description of drawings proceeds:

DESCRIPTION OF THE DRAWINGS

FIG. 5 is a top plan view of a diseased mitral valve having partially fused leaflets.

FIG. 6 is a cross-sectional end view of the embodiment of FIG. 1 positioned within the mitral valve taken along the line VI—VI of FIG. 1.

FIG. 7 is a top plan view of the mitral valve of FIG. 1 after application of our commissurotomy catheter.

FIG. 8 is a side view of a mitral valve having the embodiment of FIG. 1 positioned therein.

DESCRIPTION OF THE PREFERRED EMBODIMENTS

Figure 1:
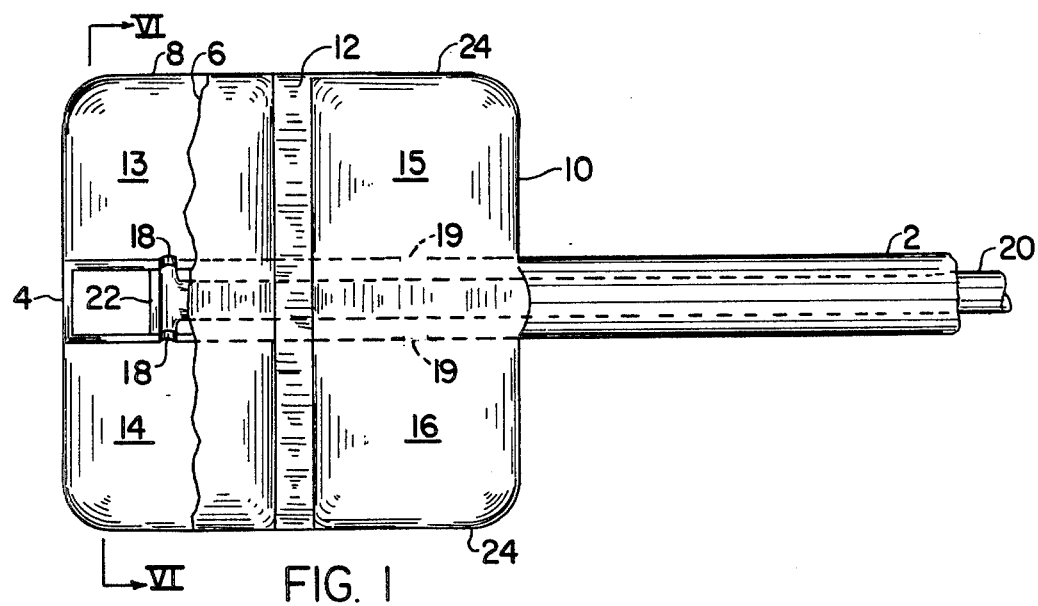
FIG. 1 is a top plan view partially in section of a present preferred embodiment of our commissurotomy catheter.
Figure 2:
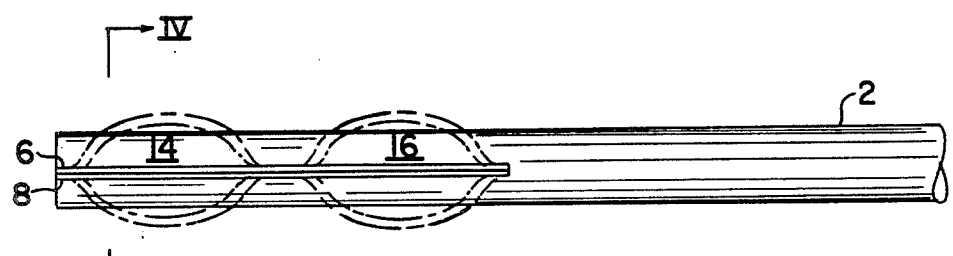
FIG. 2 is a side view of the embodiment of FIG. 1.

As shown in FIGS. 1 through 4 our commissurotomy catheter is comprised of a main lumen 2 closed at its distal end 4. A top and bottom sheet preferably of latex 6 and 8 are laminated together at their edges 10, through their center 12 and to the main lumen 2 thus defining the enclosed pockets or balloons 13, 14 15 and 16. Orifices 19 are provided in the lumen 2 so that a fluid will pass through the lumen 2 into balloons 15 and 16 to inflate them. A second lumen 20 is provided within lumen 2. End pipes 22 are provided on this lumen 20 which attach to the main lumen at orifices 18. Thus, a fluid can pass from lumen 20 through orifices 18 into balloons 13 and 14. Cutting edges 24 extend along the edges of the balloons parallel to the main lumen 2. The cutting edges may be a string made of nylon or similar material. The balloons are inflated by injecting a fluid such as saline through the lumens 2 and 20. FIG. 2 shows the catheter with the balloons 14 and 16 deflated (the solid lines) and inflated (the dotted lines).

Figure 3:
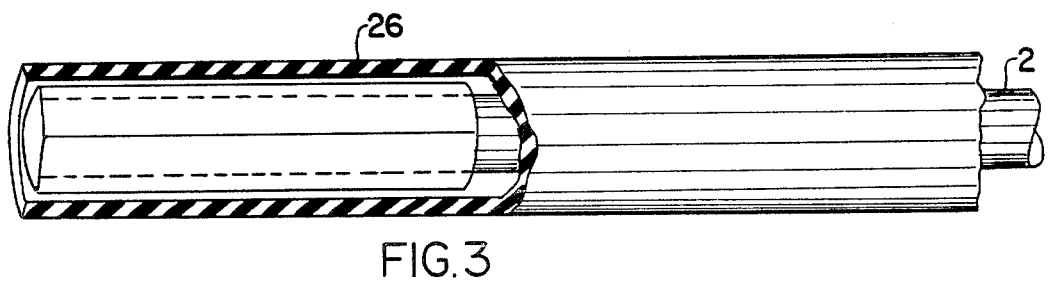
FIG. 3 is a side view, partially in section, of the embodiment of FIG. 1 prepared for insertion into the heart.
Figure 4:
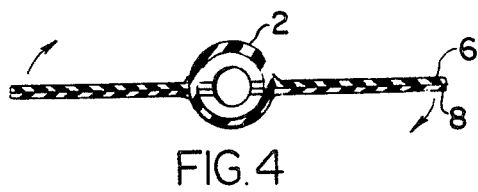
FIG. 4 is an end cross-sectional view of the embodiment of FIG. 1 taken along the line IV—IV in FIG. 2 after the balloons have been deflated.

To prepare the catheter for insertion into the heart the balloons are deflated and wrapped about the main lumen 20 as indicated by the arrows in FIG. 4. After wrapping, a cover lumen 26 is extended over the main lumen 2 until it encloses the wrapped balloons as shown in FIG. 3.

The mitral valve is comprised of two leaflets 30 and 32 extending from the heart wall 34 as shown in FIG. 5. In a diseased valve the ends of the leaflets will have fused together, as shown at 36 for example, thereby restricting the passageway 38 through which blood flows. To open the passageway 38 our commissurotomy catheter is inserted into the passageway 38 The catheter contains a radio-opaque marker to allow the surgeon or radiologist to see where it is at all times. The cover lumen 26 is retracted to expose the wrapped balloons. Then a saline solution filled with a radio-opaque medium such as Renografin is pumped into the balloons through lumens 2 and 20. This will cause the balloons to unwrap and the cutting edges 24 to align with the fissures at the fusion lines 36. As the balloons are inflated the cutting edges will press against the fused joints of the leaflets causing them to separate as shown in FIGS. 6 and 8. Should this force be insufficient to separate the leaflets, the surgeon may rhythmically inflate and deflate the balloons so that the cutting edges will vibrate or rock and saw the leaflets apart. The position of the balloons is visible on the fluoroscope due to the content of the contrast medium. After the valves have been separated the balloons are deflated, the cover is replaced and the catheter is removed. The valve will then open fully as shown in FIG. 7.

Figure 9:
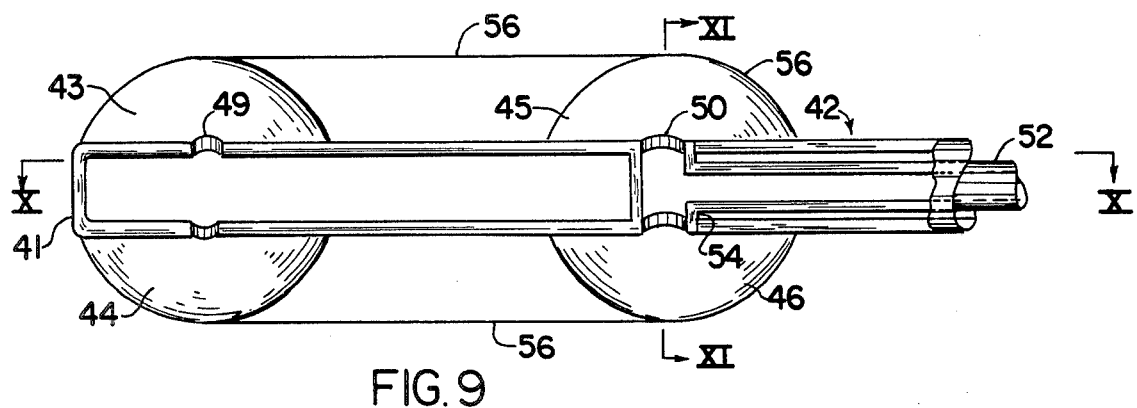
FIG. 9 is a side view partially in section of a second preferred embodiment of our commissurotomy catheter.
Figure 10:
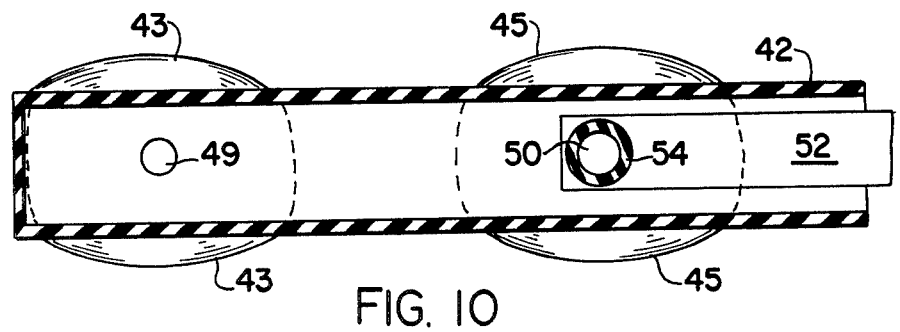
FIG. 10 is a cross-sectional view taken along the line X—X of FIG. 9.
Figure 11:
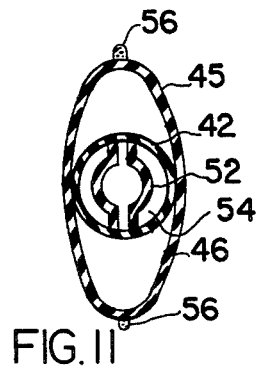
FIG. 11 is a cross-sectional end view taken along the line XI—XI of FIG. 9.

A second present preferred embodiment is illustrated in FIGS. 9, 10 and 11. As in the first embodiment a main lumen 42 with a closed end 41 is provided. Four balloons 43, 44, 45 and 46 are attached to the exterior of the main lumen 42 so that a fluid may pass through openings 49 and 50 into the balloons to inflate them. As in the first embodiment, we provide a second lumen 52 having endpipes 54 for inflating one pair of balloons 45 and 46. Cutting edges are provided by a nylon strings 56 attached to the main lumen 42.

The second embodiment is used in the same manner as the first. A cover lumen (not shown) is used for insertion of the catheter into the mitral valve. Then the cover is removed and the balloons are inflated. As the balloons are inflated the cutting edges will align with the fissures along the fused leaflets. Then the edges will press against the fusion lines causing the fused leaflets to separate. After the leaflets are separated the balloons are deflated, the cover lumen is replaced and the catheter is removed.

Figure 12:
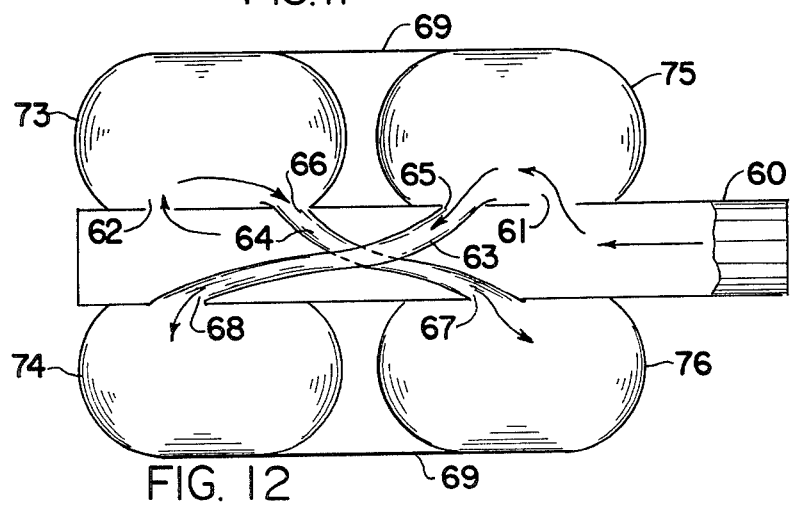
FIG. 12 is a side view partially in section of a third preferred embodiment of our commissurotomy catheter.

One could eliminate the need for a second lumen by interconnecting the balloons as shown in FIG. 12. There we provide inlets 61 and 62 which allow fluid to pass from the main lumen 60 into balloons 73 and 75. Tube 63 runs from outlet 65 to inlet 68 and interconnected balloons 74 and 75. Tube 64 runs from outlet 66 to inlet 67 and interconnects balloons 73 and 76. Nylon strings 69 attached to the lumen 60 provide cutting edges.

Figure 13:
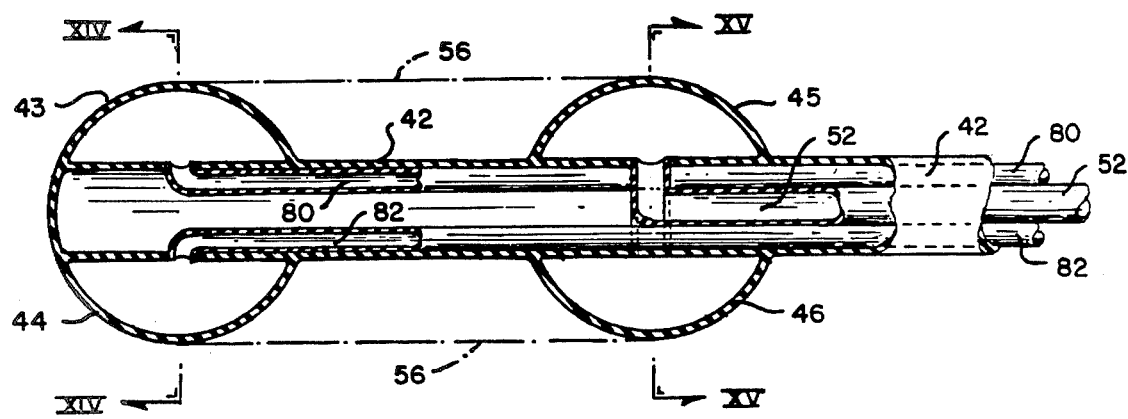
FIG. 13 is a side view similar to FIG. 9 showing a fourth preferred embodiment of our commissurotomy catheter.
Figure 14:
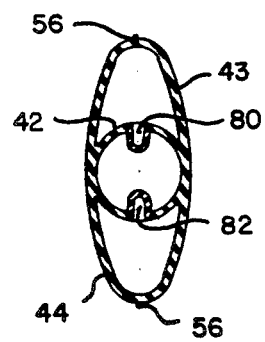
FIG. 14 is a cross-sectional view taken along the line XIV—XIV of FIG. 13.
Figure 15:
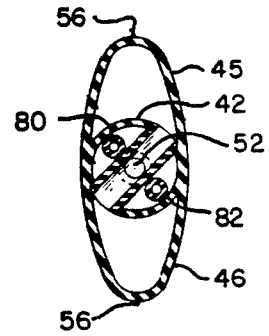
FIG. 15 is a cross-sectional view taken along the line XV—XV of FIG. 13.

The third embodiment is used in the same manner as the previous embodiments. However, saline will pass from the lumen 60 into balloons 73 and 75. Then saline in balloon 73 will flow to balloon 76 and saline from balloon 75 will flow to balloon 74. As illustrated in FIGS. 13, 14 and 15 one could provide separate lumens 80 and 82 within the main lumen 42 to inflate balloons 43 and 44. The third lumen 80 and fourth lumen 82 would permit balloons 43 and 44 to be independently inflated and deflated. In this manner the cutting edges 56 could be independently operated.

While we have shown and described certain present preferred embodiments of our invention and methods of using them it is to be distinctly understood that the invention is not limited thereto but may be variously embodied within the scope of the following claims.

We claim:
1. A commissurotomy catheter comprising
   (a) an elongated lumen having an inlet end, a first outlet and second outlet;
   (b) first inflatable means and second inflatable means attached to the lumen each positioned so that a fluid may pass from the lumen through an outlet and into the inflatable means, thereby inflating the inflatable means; and
   (c) a cutting means connected to and extending between the first inflatable means and the second inflatable means.
2. The catheter of claim 1 wherein the first and second inflatable means are comprised of a first and second sheet of elastic material joined together so as to define two separate pockets into which fluid may pass from the outlets.
3. A commissurotomy catheter comprising:
   (a) an elongated first lumen having an inlet end, and at least one outlet,
   (b) a first inflatable means attached to the first lumen in a manner so that a fluid may pass from the first lumen through an outlet and into the first inflatable means, thereby inflating the inflatable means,
   (c) a second inflatable means attached to the first lumen,
   (d) a second lumen having an inlet end and an outlet end and located within the first lumen so that its outlet end is connected to the first lumen near the outlet of the elongated first lumen, its inlet is near the inlet end of the elongated first lumen and the outlet of the second lumen is positioned so that a fluid may pass from the second lumen through its outlet and into the second inflatable means, thereby inflating the second inflatable means, and
   (d) a cutting means attached to and extending between the first and second inflatable means.

4. The catheter of claim 1 wherein the elongated lumen has a third and fourth outlet and also comprising
   (a) inflatable means positioned at the third and fourth outlets so that fluid passing through the outlets will inflate the inflatable means, and
   (b) a second cutting means extending between the third and fourth inflatable means.

5. The catheter of claim 3 also comprising a third and fourth lumen positioned within the first lumen, the third lumen being connected to the third outlet and the fourth lumen being connected to the the fourth outlet.

6. A method for separating the fused leaflets of a heart valve comprising
   (a) positioning within the heart a commissurotomy catheter comprised of
      (i) an elongated lumen having an inlet end, a first outlet and a second outlet,
      (ii) a first and second inflatable means each positioned so that a fluid may pass from the lumen through an outlet and into the inflatable means, thereby inflating the inflatable means, and
      (iii) a cutting means connected to the inflatable means so that when the catheter is properly positioned within the heart the first inflatable means is on one side of the leaflets and the second inflatable means is on the other side and the cutting means will extend through the valve,
   (b) inflating the first inflatable means
   (c) inflating the second inflatable means to force the fused leaflets apart,
   (d) deflating the first and second inflatable means, and
   (e) removing the catheter from the heart.

7. The method of claim 6 wherein the inflatable means are inflated by the injection of a saline solution.

8. The method of claim 6 wherein the first and second inflatable means are inflated in a manner so that the cutting edge between the first and second inflatable means will vibrate.

9. The method of claim 6 also comprising the step of alternately deflating and reinflating the first and second inflatable means so that the cutting edge will rock in a saw-like motion.

10. The method of claim 6 also comprising the steps of
    (a) covering the commissurotomy catheter with a cover lumen prior to and during positioning,
    (b) removing the cover lumen prior to inflating the inflatable means, and
    (c) replacing the cover lumen after deflating the inflatable means.

11. The method of claim 6 also comprising the step of introducing a radio-opaque marker to the catheter prior to positioning the catheter within the heart.

* * * * *